(12) United States Patent
Amdur et al.

(10) Patent No.: US 8,992,959 B2
(45) Date of Patent: Mar. 31, 2015

(54) ARTICLES HAVING ANTIMICROBIAL PROPERTIES AND METHODS OF MANUFACTURING THE SAME

(75) Inventors: Samuel T. Amdur, Libertyville, IL (US); Min Yao, Vernon Hills, IL (US)

(73) Assignee: Medline Industries, Inc., Mundelein, IL (US)

( * ) Notice: Subject to any disclaimer, the term of this patent is extended or adjusted under 35 U.S.C. 154(b) by 0 days.

(21) Appl. No.: 12/965,658

(22) Filed: Dec. 10, 2010

(65) Prior Publication Data

US 2012/0148651 A1    Jun. 14, 2012

(51) Int. Cl.
| | |
|---|---|
| *A01N 25/08* | (2006.01) |
| *A01N 47/44* | (2006.01) |
| *B29C 41/00* | (2006.01) |
| *A01N 25/34* | (2006.01) |
| *B29C 41/14* | (2006.01) |
| *A41D 31/00* | (2006.01) |
| *A41D 19/00* | (2006.01) |

(52) U.S. Cl.
CPC ............. *A01N 25/34* (2013.01); *B29C 41/14* (2013.01); *A01N 47/44* (2013.01); *A41D 31/0077* (2013.01); *B29C 41/003* (2013.01); *A41D 2400/34* (2013.01); *A41D 19/0055* (2013.01)
USPC .......................................... 424/409; 424/661

(58) Field of Classification Search
CPC ...................................................... A01N 25/34
USPC .................................................. 424/409, 661
See application file for complete search history.

(56) References Cited

U.S. PATENT DOCUMENTS

| | | | |
|---|---|---|---|
| 4,853,978 A | 8/1989 | Stockum | |
| 5,180,605 A | 1/1993 | Milner | |
| 5,459,879 A | 10/1995 | Fuchs | |
| 5,483,697 A | 1/1996 | Fuchs | |
| 5,486,322 A * | 1/1996 | Fuchs | ............... 264/46.5 |
| 5,487,896 A | 1/1996 | Modak et al. | |
| 5,639,295 A | 6/1997 | Wellinghoff et al. | |
| 5,708,023 A | 1/1998 | Modak et al. | |
| 5,725,867 A | 3/1998 | Mixon | |
| 5,888,441 A | 3/1999 | Milner | |
| 5,914,120 A | 6/1999 | Wellinghoff et al. | |
| 5,965,610 A | 10/1999 | Modak et al. | |
| 5,993,839 A | 11/1999 | Mixon | |
| 6,037,386 A | 3/2000 | Modak et al. | |
| 6,361,786 B1 | 3/2002 | Shanbrom | |
| 6,716,895 B1 | 4/2004 | Terry | |
| 7,262,021 B1 | 8/2007 | Taintor | |
| 7,435,429 B2 | 10/2008 | Modak et al. | |
| 7,563,461 B2 | 7/2009 | Modak et al. | |
| 7,601,731 B2 | 10/2009 | Raad | |
| 7,652,040 B2 | 1/2010 | Bosmans et al. | |
| 7,713,472 B2 | 5/2010 | Raad et al. | |
| 7,745,425 B2 | 6/2010 | Modak et al. | |
| 7,759,327 B2 | 7/2010 | Modak et al. | |
| 7,771,644 B2 | 8/2010 | Flather et al. | |
| 7,879,365 B2 | 2/2011 | Modak et al. | |
| 7,951,840 B2 | 5/2011 | Modak et al. | |
| 8,207,148 B2 | 6/2012 | Modak et al. | |
| 2005/0147655 A1 | 7/2005 | Bagwell et al. | |
| 2007/0129690 A1 | 6/2007 | Rosenblatt et al. | |
| 2007/0154621 A1 | 7/2007 | Raad | |
| 2007/0298085 A1 | 12/2007 | Lestage et al. | |
| 2008/0183152 A1 | 7/2008 | Raad et al. | |
| 2009/0099529 A1 | 4/2009 | Anderson et al. | |
| 2009/0143516 A1 * | 6/2009 | MacDonald et al. | ......... 524/236 |

FOREIGN PATENT DOCUMENTS

| | | |
|---|---|---|
| NZ | 556353 | 2/2009 |
| WO | WO 95/26134 | 10/1995 |
| WO | WO 02/082907 | 10/2002 |
| WO | WO 2004/108091 | 12/2004 |
| WO | WO 2006/074359 | 7/2006 |
| WO | WO 2007/062306 | 5/2007 |

\* cited by examiner

*Primary Examiner* — Jake Vu

(57) ABSTRACT

According to one embodiment, a coagulant comprising calcium nitrate and an antimicrobial agent is disclosed. The coagulant may be used in the molding process to releasably bond the substrate material to the mold and to bond to the antimicrobial to the substrate material.

2 Claims, 4 Drawing Sheets

ARTICLES HAVING ANTIMICROBIAL PROPERTIES AND METHODS OF MANUFACTURING THE SAME

FIELD OF THE INVENTION

The present invention relates generally to an elastic article and, in particular, to articles having antimicrobial properties.

BACKGROUND

Infections received under the care of others, particularly in locations where harmful bacteria are present and other high infection risk areas is a ubiquitous problem that leads to longer hospital stays, increased patient care cost and sometimes death. At any point of time around the world, current data indicates that approximately 1.4 million people are suffering the consequences of hospital-acquired infections (HAI). Each year, thousands of people die from HAI. In the United States alone, the number of deaths per year is approximately 99,000 (10 deaths per hour). Infections that occur in Intensive Care Units (ICU) affect more than 20% of patients, accounts for 44% of patient deaths and extend ICU stays an average of 8 days.

These numbers are staggering considering that preventative measures have been incorporated into healthcare and other products to reduce the risk of infection for some time now through antimicrobial substances and other means. Clearly these solutions are ineffective or minimally effective at best. While some solutions are available, they are impractical to implement or incompatible with the devices or the manufacturing process. Getting antimicrobial substances efficiently and though mass production into the many products come in contact with bacteria and eventually come in contact with people to date has not been possible.

One common protective measure that falls in this category is elastomeric gloves. The transmission of bacteria commonly occurs via body to body contact and most commonly from the hands of healthcare workers to a patient. The center for Disease Control and Prevention (CDC) recommends glove-use guidelines and hand hygiene actions to mitigate infection, but the effectiveness due to compliance among heath care workers inter alia is insufficient and difficult to monitor and control.

In particular to gloves, some studies show that requiring glove use actually decreases hand washing compliance and hygiene, which results in the glove being a source for cross-contamination. In a study done at Yale University, researchers found a correlation of contaminated gloves with the transmission of Acinetobacter calcoaceticus var. anitratus in an intensive care unit. Yet another study, done at Northwestern University indicates that 75% of gloves in an opened box in patient rooms were contaminated.

Previous studies demonstrate that glove contamination can come from the direct contact with patients and the environment. Existing studies show 73% of the rooms of the Methicillin-resistant *Staphylococcus aureus* (MRSA) infected patients had MRSA contamination on environmental surfaces; 65% of nurses tending the patients' wounds or urine bags contaminated their uniforms or gowns with MRSA; 42% of personnel who had no direct contact with these patients but had touched contaminated surfaces, contaminated their gloves with MRSA. Further, it is also possible that contamination can occur during manufacturing and handling before gloves are actually used by a healthcare worker.

Currently healthcare gloves and other contaminable equipment are not sterilized or treated with antimicrobials in a process that effectively produces antimicrobial results. Some have tried to incorporate antimicrobial effects into gloves and the like. In one solution, a combination of antimicrobial substances and other agents such as dyes are impregnated or sprayed onto device surfaces to enhance the antimicrobial effect. However these solutions use high concentrations of antimicrobial chemicals and are not compatible with high speed, high volume manufacturing requirements. This type of solution will waste significant amounts of the antimicrobials as the glove is worn for a short period of time. Further, organic solvents were used in the coating/impregnation solution and long drying times are required. In some cases more than 4 hours of drying time. Still further, the remaining antimicrobial in the used glove can create environment issues. As such, to achieve the desired and effective kill rate, higher concentrations of the antimicrobial and or dye are necessary, adding not only cost to the process but environmental concerns as well.

Traditionally, when manufacturing elastomeric articles, a coagulant is mixed with a powder such as calcium carbonate was used to allow the article to be easily removed from the mold. However, the calcium carbonate must be removed from the glove, generally by additional washing and drying steps, adding time and expense to the process.

Recently powder free coagulants have been developed by many glove manufacturers. These powder free coagulants greatly reduce manufacturing costs by eliminating the need to wash and dry gloves after they are manufactured. However, these are very precise mixtures and even small variations in the coagulant makeup have detrimental effects on the product outcome resulting in glove thickness variations and wasted material.

Accordingly, a need exists for protective articles and a process for making the same that can prevent or inhibit the growth of microorganisms in or on the articles from the point of manufacture.

BRIEF DESCRIPTION OF THE DRAWINGS

The foregoing and other advantages of the invention will become apparent upon reading the following detailed description and upon reference to the drawings.

Figure 1:
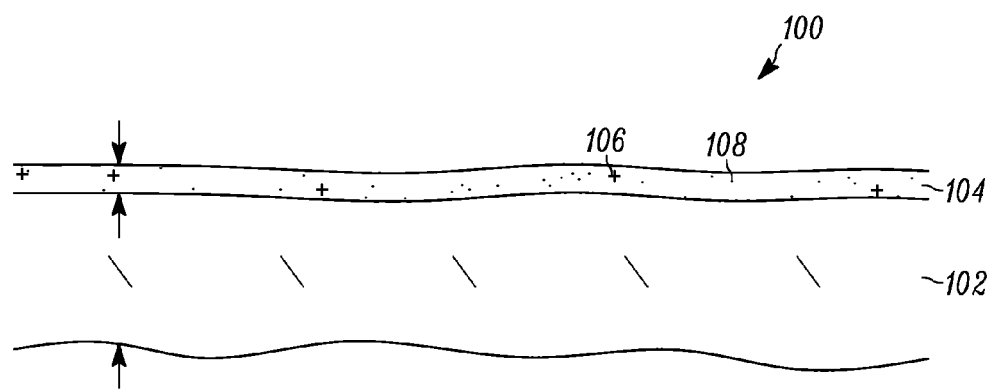
FIG. 1 illustrates a cross sectional view of substrate with an antimicrobial layer according to one embodiment.

While the invention is susceptible to various modifications and alternative forms, specific embodiments have been shown by way of example in the drawings and will be described in detail herein. It should be understood, however, that the invention is not intended to be limited to the particular forms disclosed. Rather, the invention is to cover all modifications, equivalents, and alternatives falling within the spirit and scope of the invention.

DESCRIPTION OF ILLUSTRATIVE EMBODIMENTS

A coagulant formulation that includes a powder free mold release agent and an antimicrobial agent that imparts an antimicrobial effect on the molded product is disclosed. The coagulant formulation comprising at least one antimicrobial in a first predetermined amount to achieve a predetermined kill rate on a molded article. Although the remainder of the description is directed to elastomeric articles, it is to be understood that the embodiments may also be implemented on other articles formed from a mold such as, for example, condoms, probe covers, breathing bags and the like Embodiments of the invention are now described in detail. Referring to the drawings, like numbers indicate like parts throughout the views. As used in the description herein and throughout the claims, the following terms take the meanings explicitly associated herein, unless the context clearly dictates otherwise: the meaning of "a," "an," and "the" includes plural reference, the meaning of "in" includes "in" and "on." Relational terms such as first and second, top and bottom, side and the like may be used solely to distinguish one entity or action from another entity or action without necessarily requiring or implying any actual such relationship or order between such entities or actions. Also, reference designators shown herein in parenthesis indicate components shown in a figure other than the one in discussion. For example, talking about a device (100) while discussing figure A would refer to an element, 100, shown in figures other than figure A.

Embodiments of the present invention provide a substrate that may be a wearable article, including elastomeric articles such as a glove or other outerwear, configured to include an effective amount of antimicrobial incorporated into the material from the beginning of the manufacturing process. With this invention, high kill rates are achieved with small amounts of antimicrobial with a high degree of manufacturability. This results in an evenly distributed homogenous amount of antimicrobial material on a surface of the substrate. In one embodiment, the incorporation of the antimicrobial into the article results from a mold release material. The incorporation of the antimicrobial into the article occurs prior to the drying and curing of the substrate material. In addition to wearable articles, other articles may incorporate the invention providing a highly effective antimicrobial kill rate to the article, from a minimal amount of antimicrobial agent. The discovery results in an unexpected synergistic effect between a coagulant, used in the article formation process of one embodiment, and the antimicrobial elements included in the coagulant.

Embodiments of the invention provide a coagulant solution having calcium nitrate that is picked up by the hand former in a very low amount (~0.2 gram per glove) coating the hand former mold uniformly and almost invisibly. An antimicrobial added to coagulant solution is distributed evenly on the outside of the final glove product to fight bacterial contamination.

In one embodiment, the coagulant comprises calcium nitrate and an antimicrobial which remain on the elastomeric article throughout the manufacturing process and on the final product. In one embodiment the elastomeric article is a latex glove or the like. There is an affinity between the calcium nitrate and the latex, which in this embodiment forms the elastomeric substrate, thereby leaving an evenly dispersed residual amount of the coagulant, and antimicrobial on the glove. It is to be noted that other substrate materials other than latex may be used as is understood to one of ordinary skill in the art.

Other embodiments include a process of creating an elastomeric article such as a glove, by creating a coagulant comprising a salt, a powder free agent, and an antimicrobial. The coagulant covers the mold prior to the application of the latex substrate material. The latex is applied to the mold, dried, cured and then removed from the mold. In one embodiment, the glove is removed from the mold such that the portion of the latex substrate, proximate to the mold becomes the outside of the glove. Residual amounts of the antimicrobial coagulant remain on the glove after the curing process.

Referring to FIG. 1, an article 100 comprising a substrate layer 102 and an antimicrobial coagulant layer 104 is disclosed. The anticoagulant layer 104 is a coagulant bound to the substrate from the manufacturing process. In one embodiment, the antimicrobial coagulant comprises at least one antimicrobial agent 106. In another embodiment, the antimicrobial coagulant comprises an ionic compound, an antimicrobial agent 106 and a dye 108. In yet another embodiment, the antimicrobial coagulant comprises a powder or other mold release substances.

The antimicrobial coagulant 104 may be a power free coagulant. One example of a power free coagulant is a coagulant containing stearate. In this embodiment, the stearate is evenly distributed throughout the coagulant to ensure complete release of the substrate material from the mold. The coagulant may contain calcium nitrate or other salts, for example, calcium chloride, ammonium nitrate, zinc chloride, zinc nitrate, magnesium acetate and aluminum sulphate or a combination thereof. The salts of the coagulant bond with the substrate material controlling the thickness of the substrate material. With the powder free coagulant, there is no powder to wash off of the glove as part of the process, leaving the coagulant as a consistent layer with the antimicrobial in the coagulant layer, evenly distributed over the entire glove surface.

The formulation and consistency of the coagulant are critical to ensuring consistent substrate thickness, particular in one embodiment, wherein the article is a elastomeric glove. Variations in thickness can reduce tactile characteristics, important to the wearer. This is even more important wherein the gloves are used in surgical setting. Carefully formulating and mixing the antimicrobial into the coagulant is required to not disturb the characteristics of the coagulant and its role in the substrate formation. The formulations discussed below result in the even distribution within the coagulant, the antimicrobial agents and the stearate.

Figure 2:
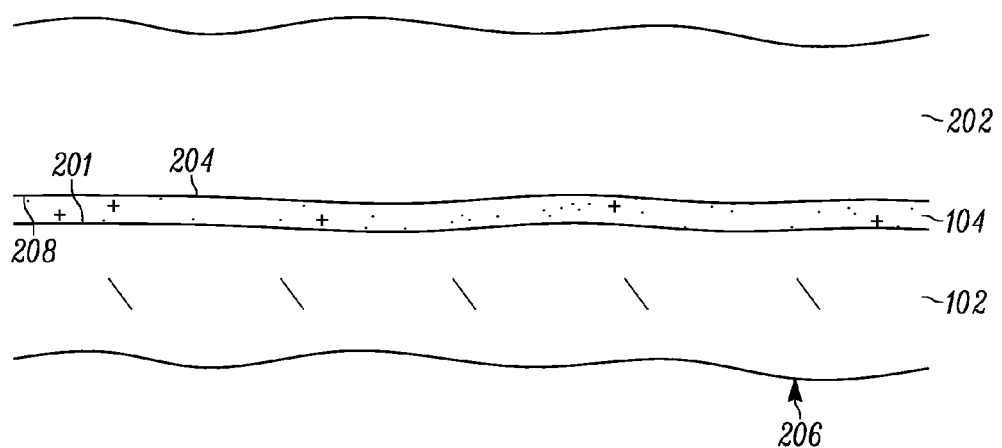
FIG. 2 illustrates a process flow diagram for forming an elastomeric article.

Referring to FIG. 2, the article 100 is shown in one embodiment on a mold 202 in cross sectional form. In this embodiment, the mold 202, also known as a former to those of ordinary skill in the art, for forming an article, has a layer of the antimicrobial coagulant 104 on a molding surface 204 prior to application of the substrate layer material in liquid form. Once the substrate layer material is applied to the mold, the coagulant resides between the mold and the substrate material layer 102. The release agent of the coagulant releasably adheres the substrate material to the mold 202, while still allowing the substrate 102 to be released, pulled off of the mold, after the article formation process is complete. The coagulant 104 further controls the amount of substrate material 102 that adheres to the mold 202, thereby controlling the thickness of the elastomeric article.

In this embodiment, the mold surface 204 is adjacent an antimicrobial coagulant proximate surface 208. The proximate substrate surface 210, is proximate to the coagulant and the mold surface 204. The mold may be made of porcelain, glass, metal or the like.

Once the article is separated from the mold, at least a portion of the antimicrobial coagulant remains with the substrate as a substantially continuous layer of one side the article. The other portion of the antimicrobial coagulant resides with the mold. In one embodiment at least some of the antimicrobial coagulant bonds with the substrate material leaving the residual amount of the coagulant bonded to the substrate material. In this embodiment, the calcium nitrate of the coagulant for example, forms bonds with the latex substrate material. The coagulant becomes part of the glove and is not removed. Because the mold is evenly covered with the evenly dispersed antimicrobial coagulant first, the latex then covers the coagulant and the resulting latex—coagulant interface is continuous over the entire surface of the article facing the mold, or the surface of the latex proximate to the mold. The distal surface of the latex 206, distal to the mold that is, is not in contact with the coagulant and therefore does not contain any coagulant. The thicknesses of the coagulant layer and the substrate layer of FIG. 1 and FIG. 2 are exaggerated for purposes of clarity and should not be taken as representative of the actual thickness or even the ratio of relative thicknesses of the two materials.

Figure 3:
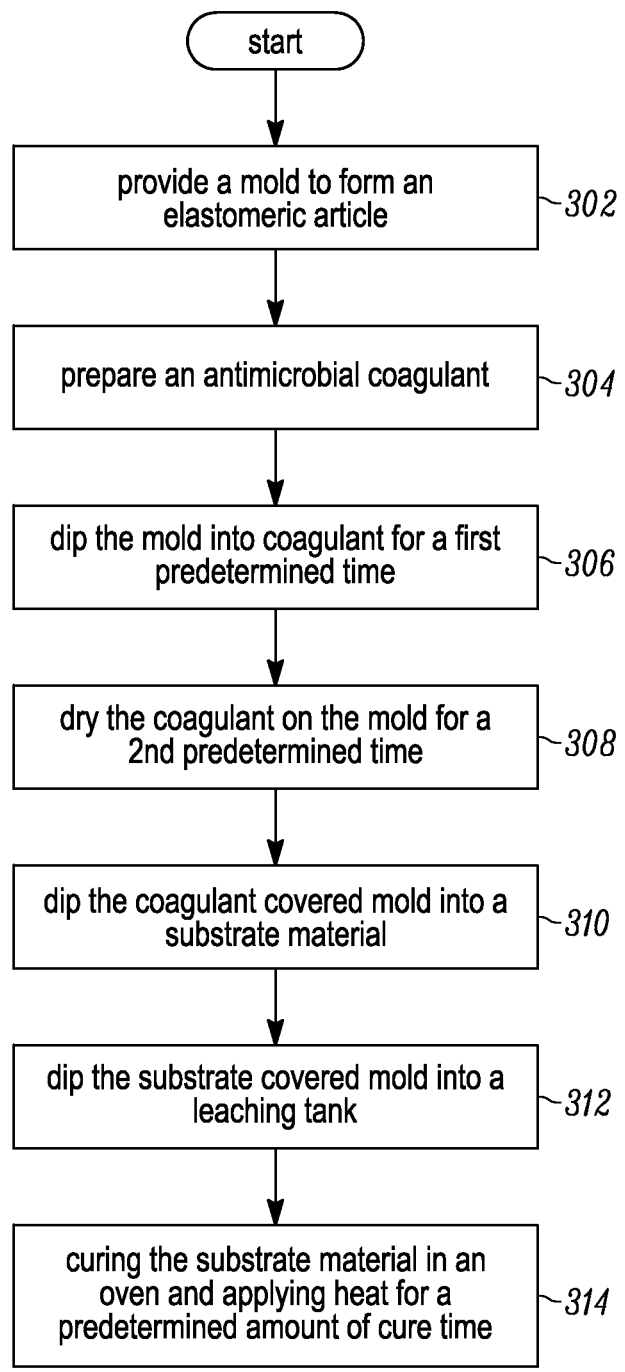
FIG. 3 illustrates an operational flow diagram for manufacturing a disposable diaper according to one embodiment.

Referring to FIG. 3, an example of one method of forming an antimicrobial article is shown. In this embodiment, the process includes providing a mold 202, which is a glove former, having a molding surface for forming an elastomeric glove. Preparing an antimicrobial coagulant 204 and providing the antimicrobial coagulant, in liquid form, in a coagulant tank. Applying the antimicrobial coagulant 206, to the mold by dipping, in this embodiment, the mold into the antimicrobial coagulant tank, coating the mold with a continuous layer of antimicrobial coagulant. The mold is inserted into the coagulant tank for a first predetermined amount of time. The liquid antimicrobial coagulant adheres to the mold. The coagulant is agitated or constantly mixed to maintain even dispersion of the antimicrobial agents, the mold release agents and the other components of the coagulant.

Because the coagulant is in a liquid state it may flow freely over the mold providing a continuous layer of coagulant over the entire molding surface including any portions of the mold with shaper angles or voids and crevices. The antimicrobial coagulant covered mold is removed from the coagulant tank. In one embodiment the coagulant is dried 208 for a predetermined period of time. In another embodiment the coagulant drying time is the time it takes to move the mold from the coagulant tank to the latex tank. In one embodiment, the amount of coagulant picked up by the mold is very low, less than 1.0 gram per article. In another embodiment, less than 0.3 grams and preferably about 0.2 grams of coagulant are applied to the mold. The amount of coagulant that is present on the mold is controlled by ion concentration and the time in the coagulant tank.

Once the coagulant is in place on the mold surface, the substrate material is introduced by applying the substrate material 210, in liquid form in this embodiment, to the coagulant covered mold. In this embodiment, liquid latex is prepared as the substrate material and provided in a liquid latex tank. The step of applying the latex to the coagulant covered mold, comprises dipping the coagulant covered mold into the tank of latex for a first predetermined time. The latex adheres to the antimicrobial coagulant, forming into the shape of the mold surface. Then removing the latex covered mold from the latex tank. The coagulant converts the liquid latex film into a wet-gel on the mold.

Introducing the latex covered mold to a leaching bath to leach impurities 214, including proteins from the latex by, in this embodiment, dipping the mold into a tank of leaching solution. In one embodiment, the leaching bath is a hot water bath. Because the coagulant is enclosed between the latex and the mold, the leaching solution does not come in contact with the antimicrobial coagulant. The article may be pre-dried subsequent to leaching. The glove may also be powdered and then may be dried. This may be air dried or the article may be passed though an oven.

The mold is removed from the leaching tank or drying stage if applied and the latex cured. Curing 212 the latex comprises heating the latex covered mold and the elastomeric article is formed. Once cured the article is leached again, in hot water in this embodiment. After one or more process treatments, treating the inside surface of the article for example, the article is removed from the mold. In one embodiment the inside surface of the article is treated with a skin conditioning substance such as aloe vera or the like.

In this embodiment, the article is peeled or rolled off of the mold such that the antimicrobial coagulant is on the outside of the article one removed. The process treatments to the inside surface of the glove are done while the glove is still on the mold in the inside out configuration. Once removed, the article may then be packaged and may also be sterilized. The resulting article is a latex glove with a coagulant film layer containing antimicrobial evenly dispersed in the coagulant film.

Surprisingly, the antimicrobial agent in combination with a dye and the coagulant, in even small residual amounts in the glove, has a significant antimicrobial effect, using a minimal amount of both the dye and the antimicrobial material. In fact, and even more surprising, as the dye concentration increases, although there is at first an increase in the antimicrobial effect, i.e. an increase in the kill rate, however, as the concentration of dye is further increased, the antimicrobial effect decreases, i.e. the kill rate, decreases. This indicates that increasing the dye concentration results in a decrease in the effective kill rate with an antimicrobial coagulant substrate combination. This is surprising as other methods, such as applying the antimicrobial and dye system, requires higher concentrations in order to achieve desirable microbe kill rate.

To state this a different way, as the concentration of the dye increases in concentration, beyond the point at which it provides the most effective kill rate, the kill rate rapidly decreases. This indicates that simply adding more dye, i.e. higher concentration of brilliant green dye in this embodiment, reduces the synergistic effect of the brilliant green, antimicrobial, coagulant combination. In one particular embodiment, the brilliant green molecules are smaller in size compared to the CHG, as the brilliant green concentration is increased CHG effectiveness is decreased, and the brilliant green blocks access for CHG to the microbes as the brilliant green covers a greater surface area.

Figure 4:
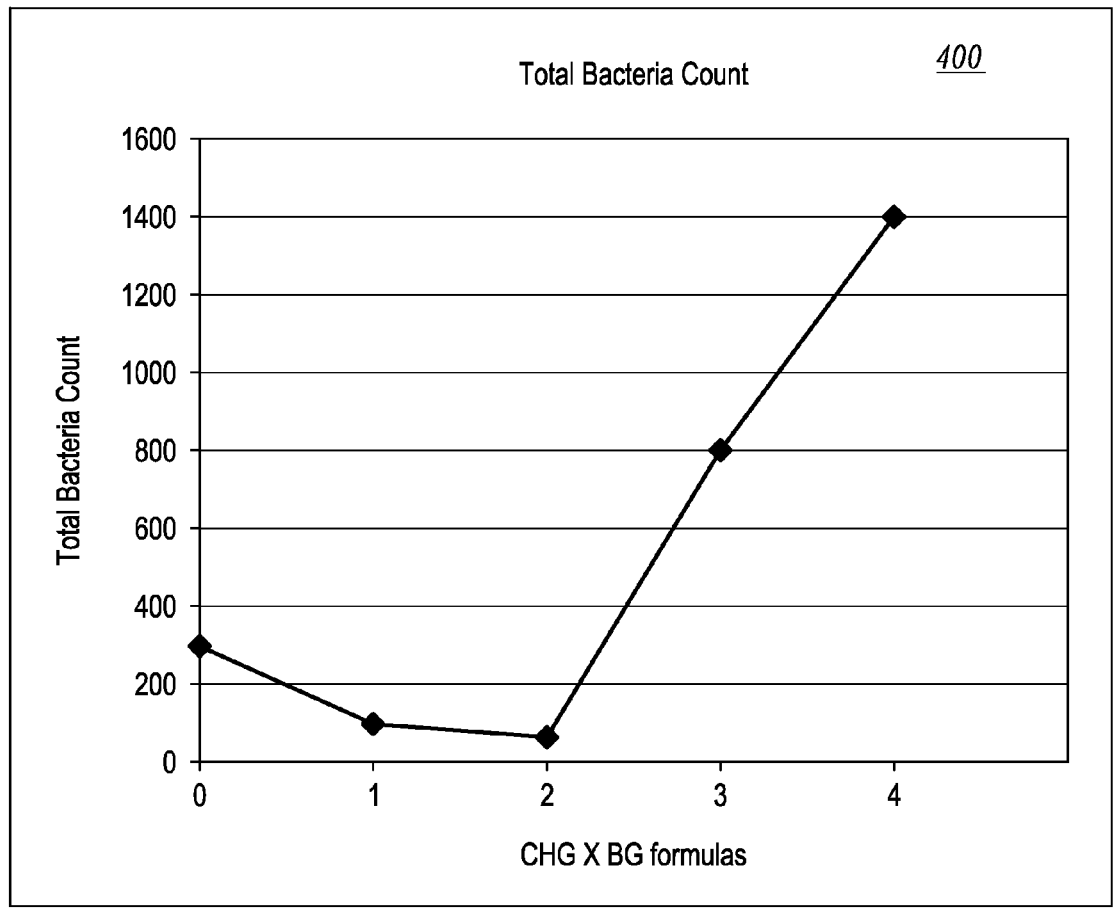
FIG. 4, illustrates a chart of the effective kill rate versus combinations of different concentrations of antimicrobial.

Referring to FIG. 4, the effective kill rate versus combinations of different concentrations of antimicrobial and dye is illustrated in the chart 400. The chart 400 illustrates that increasing the amount of brilliant green reverses the kill rate trend at inflection point 302. In this embodiment, the coagulant solution containing antimicrobial was prepared by mixing 0.048 gram of brilliant green and 3.6 gram of CHG together. First, 0.048 g of brilliant green was dissolved in 3.0 liters of soft water. The solution was stirred until brilliant green was dissolved completely. Then 3.6 grams of CHG was added to brilliant green solution and mixed well. Next, 3.0 L of coagulant solution was prepared at double concentration. Then, the 3.0 liter(L) of CHG plus brilliant green solution was added to 3.0 L coagulant solution to form 6 L of coagulant solution containing an evenly dispersed amount of CHG (0.012%) and an evenly dispersed amount of brilliant green (0.008 mg/ml). As a result of the low concentrations of the antimicrobial and the dye, the coagulant system was not disturbed and there were no precipitates. This is important as the coagulant mixture and its consistency, as discussed above, has a significant effect on the resulting article characteristics. Further the even dispersion of the antimicrobial agents in the coagulant is important as this results in the even distribution of the resulting antimicrobial effect on the finished article. The same steps were repeated for Formula 2, Formula, 3 and Formula 4 mixtures, with the different concentrations of the dye and the antimicrobial; the complete table follows:

TABLE 1

Antimicrobial and dye formulation

|  | Brilliant Green Mg/ml | CHG % |
|---|---|---|
| Formula 1 | 0.008 | 0.012 |
| Formula 2 | 0.008 | 0.024 |
| Formula 3 | 0.080 | 0.012 |
| Formula 4 | 0.080 | 0.024 |

In order to determine the effectiveness of the antimicrobial coagulant on a finished article, a total bacterial count test was completed on the article prepared using the above formulas. The following three concentrations were prepared: 0.8% Saline Solution (sodium Chloride), 4% TSA & 6.5% SDA solution, which were subsequently sterilized at 121° C. for 15 minutes. Three gloves made with each formula were cut into two pieces each and were soaked into 60 ml Saline solution and shaken for 10 minutes. After that, 1 ml of the solution and 1 ml of Agar solution (TSA and SDA) were pipetted out into a Petri dish. The Petri dish plates were incubated for 2 days at 30-35° C. for TSA & 4 days at 20-25° C. for SDA. The colonies on each plate was counted and total fungus/aerobic bacteria count per glove was calculated as:

Total Aerobic Bacteria Count Per Glove=(Count of TSA plate*60)/3

Total Fungus Count Per Glove=(Count of SDA plate*60)/3

The results of total bacteria count on TSA for above four samples and control sample are listed below.

TABLE 2

Bacteria Counts

| Set | Total Bacteria Count On TSA | Percentage of Reduction |
|---|---|---|
| Control | 300 | 0 |
| 1 | 90 | 70% |
| 2 | 60 | 80% |
| 3 | To Many To Count | 0 |
| 4 | To Many To Count | 0 |

Figure 5:
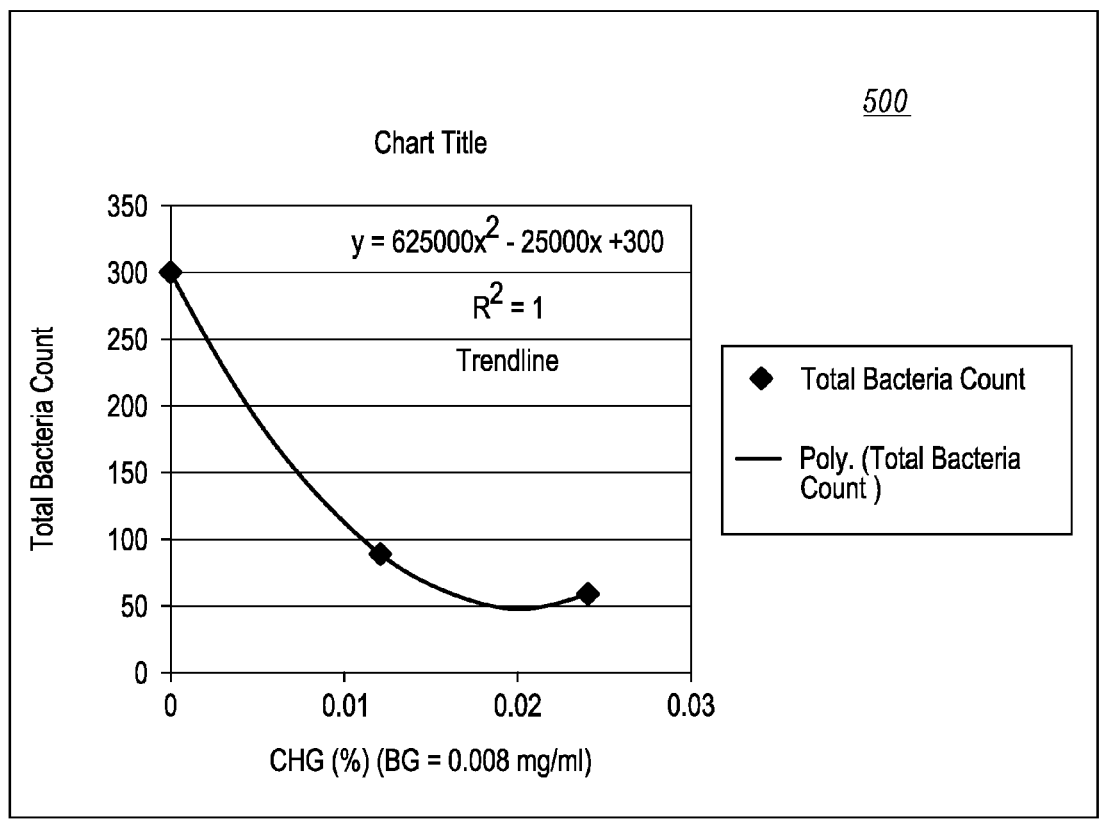
FIG. 5, illustrates another chart of the effective kill rate versus combinations of different concentrations of antimicrobial.

Referring to FIG. 5, the total bacteria count on the prepared articles, as a function of the concentration of the CHG antimicrobial is illustrate in the chart 500. As the concentration of CHG increased from a level of 0.0 percent, the amount of bacterial decreased up until an amount of CHG reached approximately 0.02 percent. As the concentration of CHG increases above 0.02 percent, the total bacteria count surprisingly began to increase.

Articles of elastomeric nature in past solutions have exhibited a leaching out of the antimicrobial agent from the article. The Kirby-Bauer test is used to indicate the amount of bacterial growth around the article. Any lack of growth to objects adjacent to the article shows that antimicrobial agents leached out of the article and inhibited such growth; know as a zone of inhibition. With the articles produced using the four different formulations of antimicrobial coagulant, there was no zone of inhibition present. Explained differently, there was no bacterial growth under the treated sample, which means the treated sample killed all bacteria on contact, but not beyond. The antimicrobial coagulant formed article is a non leaching article wherein there is non zone of inhibition.

Further tests for Antimicrobial Performance Evaluation Use the JIS 2801 Test Method. In this test, Japanese Industrial Standard Z 2801: 2000 (Antimicrobial products—Test for antimicrobial activity and efficacy) was used. The challenging microbe was MRSA (Methicillin-resistant *Staphylococcus aureus*) (ATCC #33591). The culture was maintained lyophilized and working stock culture was transferred monthly. The storage temperature was 2-8° C. The test organism (MRSA) was inoculated from the stock culture and incubated at 37±2° C. for 18-24 hours before testing. The concentration of microbial suspension was adjusted to be $2.2 \times 10^6$ CFU/ml. In this study, a sterile PE film that did not support microbial growth was used as the control. A glove formed with the antimicrobial coagulant was tested in duplicate replicates. Sample was cut into a square of 40 mm×40 mm prior to testing. The sample and control were placed into sterile Petri dishes with the test surface facing up. 0.4 ml of MRSA solution was pipetted onto the test surface and covered with a sterile thin film gently pressing down to spread the test inoculum over the film, without any spilling over the edge. The sample and control Petri dishes were incubated for 1 minute and 10 minutes. At each sampling interval, inoculated test sample was placed in a flask containing 100 ml of neutralizer. The test bacteria were carefully removed from treated glove sample and film. The serial dilutions of extraction solution were placed on SCDA plates and incubated recovery plates at 37±2° C. for 48 hours.

The percentage of reduction and log reduction were calculated using the following formula:

$$R=100(C-S)/C$$

Log Reduction=Log $C$–Log $S$

R=10% reduction

C=the number of organisms recovered from the inoculated untreated control at 0 hour S=the number of organisms recovered from the inoculated treated test sample after exposure for the desired contact period

TABLE 3

Bacteria reduction results

| | | glove | | Control | |
|---|---|---|---|---|---|
| Sample ID | Organism | 1 minute | 10 minutes | 1 minute | 10 minutes |
| AM Glove | MRSA | 3.68 log >99.9% | >4.04 log >99.99% | −0.04 log No reduction | −0.06 log No reduction |

The results of table 3 show that in the 1 minute time sample, a greater than 99.9 percent reduction in bacteria occurred and a greater than 99.99 percent reduction occurred in the 10 minute sample. The results were attained with the use of the antimicrobial coagulant in the elastomeric article formation process, the coagulant containing an antimicrobial agent at 0.24% concentration and a dye at 0.008 mg/ml concentration.

Other antimicrobials may be used as the antimicrobial agent as the effect of the antimicrobial agent is to prevent or substantially minimize the risk of microbe-related effects by either killing or inhibiting the growth of microbes such as bacteria, microbial pathogens, fungi, and viruses. Not all antimicrobial agents can kill or inhibit the growth of all microbes. Rather, any one particular antimicrobial agent generally has a range of microbe types that the antimicrobial agent is effective against. As such, a variety of antimicrobial agents and/or combinations of antimicrobial agents may be included with the coagulant to provide protection against a broad range of microbes. Non-limiting examples of suitable antimicrobial agents for use in the embodiments described herein include iodine and its derivatives, cationic antimicrobial polymers (e.g., polyhexamethylene biguanide (PHMB)), mono- or poly-quaternary ammonium salt (QAS) based antimicrobials (e.g., trialkoxysilyl quaternary ammonium salt, 3-trimethoxy-silyl-propyldimethyloctadecyl ammonium chloride and its hydrolyzed product, polyquat-1, polyquat-6), chlorinated phenoxy-based antimicrobials (e.g., triclosan), pyrithione based antimicrobials (e.g., zinc pyrithione), cationic polysaccharides (e.g., chitosan), aminopolysaccharides (e.g., chitin or chitosan derivatives), benzalkonium compounds (e.g., benzalkonium chloride, and a mixture of benzalknoium chloride with metal salts such as, silver nitrate), nitro compounds (e.g., 5-nitrofurylacrolein), dimethylbenzylammonium chloride, chlorhexidines (e.g., chlorhexidine, chlorhexidine acetate, chlorhexidine gluconate, chlorhexidine hydrochloride), crosslinked polyethylene glycols and polyethylene glycols of differing molecular weights, hydantoin derivatives with halamine bond, antibiotics (e.g., polymycine, neomycin, kanamycin, grisofulvien), natural extracts with antimicrobial properties (e.g., grape fruit seed, hops, tea oil, aloe, thyme, rosemary, peppermint, basil, ginger), metallic materials in the form of metals (e.g., silver, copper and zinc materials and their oxides and salts), metal oxides (e.g., zinc oxide, silver oxide), metal salts (e.g., silver chloride, silver nitrate), metal complexes (e.g., silver-zinc zeolite), organo-metallics (e.g., tributylin maleate), combinations thereof or the like. An additional example of a suitable antimicrobial agent is Haloshield® technology manufactured by Medline Inc., which is currently headquartered at One Medline Place, Mundelein, Ill. 60060 or HaloSource Inc., which is currently headquartered at 1631 220$^{th}$ Street SE, Bothell, Wash. 98021.

Generally, antimicrobial agents are classified as antibacterial agents (e.g., antibiotics, disinfectants, and antiseptics), antifungal agents, and antiviral agents depending upon the primary use of the particular agent. For example, if an antimicrobial agent is primarily used to target fungi, the antimicrobial agent may be referred to as an antifungal agent. However, it is to be understood that these classifications are non-limiting. For example, an antibacterial agent may be effective against fungi and an antifungal agent may be effective against bacteria. Therefore, it is to be understood that the coagulant may include any combination of antibacterial agent(s), antifungal agent(s), and/or antiviral agent(s). Other dyes that may be used may include crystal violet or other staining agents, alone or in a combination thereof genetian violet, crystal violet, ethyl violet, triarylmethane dye, or other types of a monoazo dye, a diazo dye, an indigoid dye, a xanthene or a fluorescein dye, an anthraquinone dye, an anthraquinone dye, an FD&C dye or a D&C dye. Other substrate materials may be nitrile, Latex, Vinyl, Nitrile, PVC, PE, Polyisoprene, Neoprene, Polychloriprene.

It is more efficient to add antimicrobial agents and a dye to the coagulant because this portion of the glove is very thin compared to the main substrate (latex). The substrate material layer in many cases is much thicker than the antimicrobial coagulant layer, thereof adding the antimicrobial to the substrate would consume substantially more antimicrobial. Because the coagulant layer is thin compared to the substrate much less antimicrobial is used. Additionally, antimicrobial material is inactive as it remains internal and completely encapsulated within the substrate material. With the invention, the antimicrobial is incorporated into the surface of the substrate, with the bonded coagulant film layer, a greater percentage of the antimicrobial is effective.

Up until recently, powder was added to the coagulant in some cases for example calcium carbonate, that allowed the article to be easily removed. The calcium carbonate must be washed from the glove also removing at least a portion of the coagulant. An antimicrobial coagulant that is powder free, i.e. free of calcium carbonate in one embodiment, does not require the rinsing step, leaving the antimicrobial coagulant in tact on the glove.

In one embodiment, the antimicrobial coagulant is bonded to one side of the substrate material. As part of the process, the antimicrobial coagulant becomes the outside surface, as the article is removed from the form. This is an added benefit as the antimicrobial of the coagulant will into come in contact with the wearer's skin. Because the wearer has the article on for extended periods of time, in a healthcare setting for example, in comparison with intermittent touching of a patient's skin for example, the healthcare worker is not exposed to the antimicrobial for extended periods of time.

Incidentally, because the antimicrobial agent(s) can have a negative impact on the environment, reducing the quantity or concentration of the antimicrobial agent(s) in the products also lessens the environmental impact of products discarded in landfills.

While the present invention has been described with reference to one or more particular embodiments, those skilled in the art will recognize that many changes may be made thereto without departing from the spirit and scope of the present invention. Each of these embodiments and obvious variations thereof is contemplated as falling within the spirit and scope of the invention, which is set forth in the following alternative embodiments.

We claim:

1. A method of producing an antimicrobial containing coagulant comprising:
    mixing a dye and an antimicrobial together by dissolving in 3.0 liters of soft water, less than 1 gram of dye;
    stirring the mixture until the dye is substantially dissolved;
    adding less than 4 grams of antimicrobial to the dye solution and mixing the solution forming an antimicrobial dye solution;
    preparing 3.0 L of coagulant solution at double concentration; and
    adding 3.0 liter(L) of the antimicrobial dye solution to the 3.0 L of coagulant solution to form 6 L of coagulant solution containing an evenly dispersed amount of antimicrobial and an evenly dispersed amount of dye.

2. A method of producing an antimicrobial containing coagulant comprising:
    mixing 0.048 gram of brilliant green in 3.0 liters of soft water;
    stirring the mixture until the brilliant green was substantially dissolved completely;
    adding 3.6 grams of chlorhexidine gluconate to the brilliant green solution and mixing the solution;
    preparing 3.0 L of coagulant solution at double concentration; adding 3.0 liter(L) of the chlorhexidine gluconate and brilliant green solution to the 3.0 L of coagulant solution to form 6 L of coagulant solution containing an evenly dispersed amount of chlorhexidine gluconate (0.012%) and an evenly dispersed amount of brilliant green (0.008 mg/ml).

* * * * *